United States Patent [19]

Albert et al.

[11] Patent Number: 5,032,495
[45] Date of Patent: Jul. 16, 1991

[54] TETRAAZAPORPHYRINS AND OPTICAL RECORDING MEDIUM

[75] Inventors: Bernhard Albert, Maxdorf; Peter Neumann, Mannheim; Rolf-Dieter Kohler, Edingen-Neckarhausen, all of Fed. Rep. of Germany

[73] Assignee: BASF Aktiengesellschaft, Ludwigshafen, Fed. Rep. of Germany

[21] Appl. No.: 395,576

[22] Filed: Aug. 18, 1989

[30] Foreign Application Priority Data

Sep. 2, 1988 [DE] Fed. Rep. of Germany ....... 3829851

[51] Int. Cl.$^5$ .................. G11B 7/24; C09B 47/00
[52] U.S. Cl. .................. 430/495; 430/270; 430/945; 540/123; 540/124; 540/125; 540/128
[58] Field of Search ........... 430/270, 495, 945; 540/123, 124, 125, 126, 127, 128

[56] References Cited

U.S. PATENT DOCUMENTS

| | | | |
|---|---|---|---|
| 3,094,536 | 6/1963 | Kenney et al. | 540/128 |
| 4,458,004 | 7/1984 | Tanikawa . | |
| 4,492,750 | 1/1985 | Law et al. . | |
| 4,605,607 | 8/1986 | Nikles et al. . | |
| 4,657,554 | 4/1987 | Reinert et al. | 540/123 |
| 4,814,256 | 7/1987 | Aldag . | |

FOREIGN PATENT DOCUMENTS

| | | |
|---|---|---|
| 13453 | 9/1979 | European Pat. Off. . |
| 90282 | 9/1983 | European Pat. Off. . |
| 171045 | 2/1986 | European Pat. Off. . |
| 191215 | 8/1986 | European Pat. Off. . |
| 191970 | 8/1986 | European Pat. Off. . |
| 198140 | 10/1986 | European Pat. Off. . |
| 203826 | 12/1986 | European Pat. Off. . |
| 204876 | 12/1986 | European Pat. Off. . |
| 254553 | 7/1987 | European Pat. Off. . |
| 3622590 | 1/1987 | Fed. Rep. of Germany . |
| 82093 | 5/1982 | Japan . |
| 35545 | 7/1985 | Japan . |

OTHER PUBLICATIONS

CRS Press, Inc., Boca Raton, Fla. 1983, F. H. Moser et al., "The Phthalocyanines".
J. Am. Chem. Soc., 1984, vol. 106, pp. 7404–7410.
Z. Chem., vol. 26, pp. 217–218, 1986.
Patent Abstracts of Japan, vol. 11, Nr. 158(M-591)(2605), May 22, 1987; & JP-A-61 291 187 (Mitsubishi Chem. Ind. Ltd.) 20, 12, 1986.

*Primary Examiner*—Charles L. Bowers, Jr.
*Assistant Examiner*—Mark R. Buscher
*Attorney, Agent, or Firm*—Oblon, Spivak, McClelland, Maier & Neustadt

[57] ABSTRACT

An optical recording medium contains tetraazaporphyrins of the formula

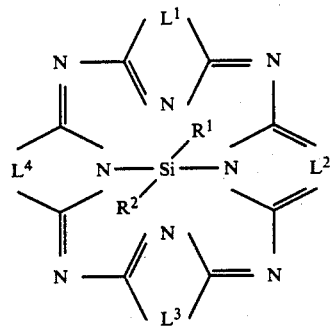

where
$L^1$, $L^2$, $L^3$ and $L^4$ are each independently of the others the radical of a bicyclic aromatic heterocycle containing 1 to 3 identical or different heteroatoms selected from the group consisting of N, O and S, which may be substituted, and
$R^1$ and $R^2$ have defined meanings.

2 Claims, No Drawings

TETRAAZAPORPHYRINS AND OPTICAL RECORDING MEDIUM

The present invention relates to novel tetraazaporphyrins of the formula I

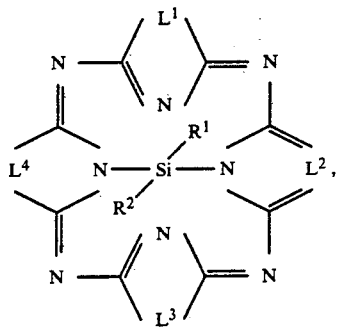

where $L^1$, $L^2$, $L^3$ and $L^4$ are identical or different and each is independently of the others a radical of a bicyclic aromatic heterocycle of 1, 2 or 3 identical or different heteroatoms selected from the group consisting of N, O and S, which may be substituted, and $R^1$ and $R^2$ are identical or different and each is independently of the other hydroxyl, $C_1$–$C_{20}$-alkoxy, $C_1$–$C_{20}$-alkyl, $C_2$–$C_{20}$-alkenyl, $C_3$–$C_{20}$-alkenyloxy or a radical of the formula II

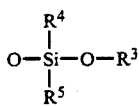

where $R^3$ is $C_4$–$C_{20}$-alkyl, $C_4$–$C_{20}$-alkenyl or phenylsubstituted $C_1$–$C_{20}$-alkyl, and $R^4$ and $R^5$ are identical or different and each is independently of the other $C_1$–$C_{12}$-alkyl or $OR^3$, where $R^3$ is as defined above, and to an optical recording medium which contains the novel tetraazaporphyrins.

Recording materials which on irradiation with rays of high energy density, for example laser light, undergo a local change of state are known. This thermally initiated change of state, for example vaporization, change of flow characteristics or fading, entail a change in the optical properties, for example the reflection or absorption, through a change in the absorption maximum or the extinction, which can be utilized for information or data recording.

Suitable light sources for an optical recording medium are for example semiconductor lasers which emit light in the near infrared. Of these it is the solid state injection lasers, especially the AlGaAs laser, which operates within the wavelength range from about 650 to 900 nm, which are particularly notable. There is therefore particularly interest in those recording materials which absorb radiation within the wavelength range from about 650 to 900 nm and are processible into thin, homogeneous layers.

The radiation-sensitive substances which find utility in optical recording systems also include IR dyes. There are for example optical storage systems which contain phthalocyanines or naphthalocyanines as radiation-sensitive components (DE-A- 3,622,590, EP-A-13,453, EP-A-203,826, U.S. Pat. No. 4,458,004, U.S. Pat. No. 4,492,750, JP-A-82,093/1982, JP-A-35,545/1985, EP-A-191,970, EP-A-191,215, EP-A-204,876, EP-A-198,140 and U.S. Pat. No. 4,605,607).

It is an object of the present invention to provide novel radiation-sensitive products which are strongly reflective and absorptive in the wavelength range of the semiconductor laser used. We have found that this object is achieved by the above-defined tetra azaporphyrins of formula I.

All the alkyl and alkenyl groups appearing in the tetraazaporphyrins according to the invention can be not only straight-chain but also branched.

The bicyclic aromatic heterocycles from which the radicals $L^1$, $L^2$, $L^3$ and $L^4$ are derived have from 1 to 3, preferably 1 or 2, identical or different heteroatoms selected from the group consisting of N, O and S, and may be substituted. The rings of this bicyclic system each have in general 5 or 6 ring members.

If the bicyclic aromatic heterocycle is substituted, each bicycle may in general have from 1 to 4 substituents (hereafter referred to as X).

Suitable substituents X are for example $C_1$–$C_{20}$-alkyl, which may be phenyl-substituted, $C_2$–$C_{20}$-alkenyl, $C_1$–$C_{20}$-alkoxy, which may be phenyl-substituted, fluorine, chlorine and bromine.

Examples of the structures from which the radicals $L^1$, $L^2$, $L^3$ and $L^4$ are derived are the basic structures of bicyclic aromatic heterocycles below. These systems may each, as stated above, be mono-, di-, tri- or tetrasubstituted by X.

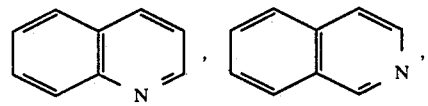

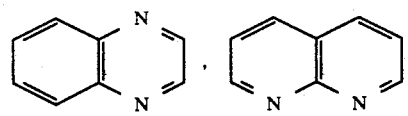

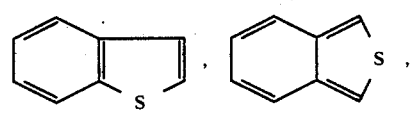

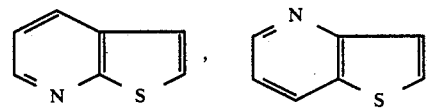

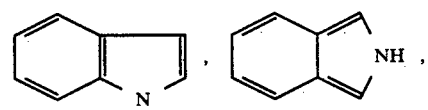

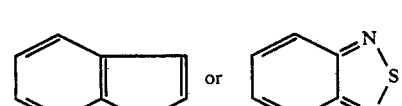

$R^1$, $R^2$, $R^4$, $R^5$ and X are each for example methyl, ethyl, propyl or isopropyl.

$R^1$, $R^2$, $R^4$, $R^5$ and X are each further for example, like $R^3$, butyl, isobutyl, sec-butyl, tert-butyl, pentyl, isopentyl, neopentyl, tert-pentyl, hexyl, 2-methylpentyl, heptyl, octyl, 2-ethylhexyl, isoocytyl, nonyl, isononyl, decyl, isodecyl, undecyl or dodecyl.

$R^1$, $R^2$, $R^3$ and X are each further for example tridecyl, 3,5,5,7-tetramethylnonyl, isotridecyl, tetradecyl, pentadecyl, hexadecyl, heptadecyl, octadecyl, nonadecyl or eicosyl. (The foregoing designations isooctyl, isononyl, isodecyl and isotridecyl are trivial names derived from the alcohols obtained by the oxo process—cf. Ullmann's Enzyklopädie der technischen Chemie, 4th edition, volume 7, pages 215–217, and volume 11, pages 435 and 436.)

$R^1$, $R^2$ and X are each further for example methoxy, ethoxy, propoxy, isopropoxy, butoxy, isobutoxy, pentyloxy, hexyloxy, heptyloxy, octyloxy, 2-ethylhexyloxy, isooctyloxy, nonyloxy, isononyloxy, decyloxy, isodecyloxy, undecyloxy, dodecyloxy, tridecyloxy, isotridecyloxy, tetradecyloxy, pentadecyloxy, hexadecyloxy, heptadecyloxy, octadecyloxy, nonadecyloxy, eicosyloxy, vinyl or allyl.

$R^1$, $R^2$ and X are each further for example, like $R^3$, methallyl, but-3-en-1-yl, undec-10-en-1-yl, octadec-9-en-1-yl, octadec-9,12-dien-1-yl,octadec-9,12,15-trien-1-yl, eicos-9-en-1-yl or eicos-5,8,11,14-tetraen-1-yl.

$R^1$ and $R^2$ are each further for example allyloxy, methallyloxy, but-3-en-1-oxy, undec-10-en-1-oxy, octadec-9-en-1-oxy, octadec-9,12-dien-1-oxy, octadec-9,12,25-trien-1-oxy, eicos-9-en-1-oxy or eicos-5,8,11,14-tetraen-1-oxy.

Phenyl-substituted $C_1$–$C_{20}$-alkyl X or $R^3$ is for example benzyl or 1- or 2-phenylethyl.

X is further for example benzyloxy or 1- or 2-phenylethoxy.

The tetraazaporphyrins according to the invention can be obtained by conventional methods as used in the preparation of phthalocyanines or naphthalocyanines and as described for example in F. H. Moser, A. L. Thomas, "The Phthalocyanines", CRC ress, Boca Rota, Florida, 1983, and J. Amer. Chem. Soc. 106 (1984), 7404–10.

Furthermore, Z. Chem. 26 (1986), 217–18, describes the preparation of tetra[2,3-quinoxaline]tetraazaporphinato-oxovanadium starting from 2,3-dicyanoquinoxaline.

The starting material for the tetraazaporphyrins of the formula I according to the invention is advantageously a dinitrile of the formula III

(III)

or a diiminoisoindoline compound of the formula IV

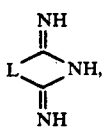
(IV)

where L is in each case d in the same way as $L^1$, $L^2$, $L^3$ and $L^4$ above and substituents capable of tetraazaporphyrin formation are each in the ortho position.

For example, the diaminoisoindolines of the formula IV are reacted with chlorosilanes of the formula V $YSiCl_3$    (V), where Y is $C_1$–$C_{20}$-alkyl, $C_2$–$C_{20}$-alkenyl or chlorine, in an inert organic diluent in the presence of a base at from 170° to 250° C. to give tetraazaporphyrins of the formula VIa

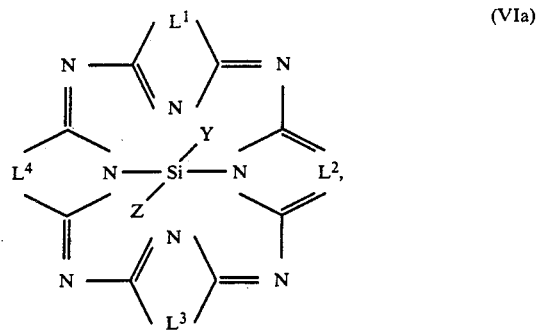

where Z is chlorine and $L^1$, $L^2$, $L^3$, $L^4$ and Y are each as defined above.

Suitable diluents are for example tetralin and nitrobenzene. Suitable bases are for example tertiary amines, such as tributylamine, quinoline, picolines or collidines.

By reacting the compounds of the formula VIa with $C_1$–$C_{20}$-alkanols or $C_3$–$C_{20}$-alkenols at from 30° to 120° C. it is possible to arrive at those compounds of the formula I where $R^1$ and/or $R^2$ are each $C_1$–$C_{20}$-alkoxy or $C_3$–$C_{20}$-alkenoxy.

However, the chlorosilicon derivative VIa can also be converted with concentrated sulfuric acid or with aqueous bases, such as sodium solution, potassium solution or aqueous ammonia solution, in the presence or absence of pyridine, at from 5° to 80° C. into the corresponding hydroxy compounds of the formula VIb. The formula VIb is identical to the formula VIa except that Y in the former is $C_1$–$C_{20}$-alkyl, $C_2$–$C_{20}$-alkenyl or hydroxyl. Z is likewise hydroxyl.

By reacting the hydroxy compound VIb first with chlorosilanes of the formula VII

where $Q^1$ and $Q^2$ are identical or different and each is independently of the other $C_1$–$C_{12}$-alkyl or chlorine, in pyridine in the presence of sodium hydride at from 15 to 150° C. and then with alcohol of the formula VIII $R^3$—OH    (VIII), where $R^3$ is as defined above, at from 30° to 120° C. it is finally possible to arrive at the tetraazaporphyrins of the formula I according to the invention.

The novel tetraazaporphyrins of the formula I show high molar absorption in the near infrared. They form homogeneous, amorphous layers and/or are advantageously incorporable into dye-in-polymer layers.

It is a further object of the present invention to provide a novel optical recording medium in which the layers which contain the novel products should be homogeneous, should show good adhesion to customary base materials and should be stable over a prolonged period.

We have found that this object is achieved by an optical recording medium comprising a base and a radiation-sensitive layer, wherein the radiation-sensitive layer contains a tetraazaporphyrin of the formula I

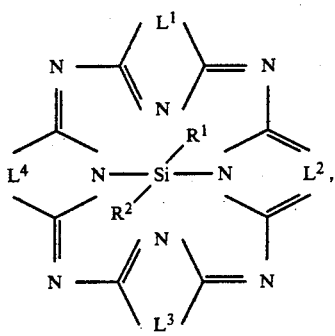

where $L^1$, $L^2$, $L^3$ and $L^4$ are identical or different and each is independently of the others the radical of a bicyclic aromatic heterocycle of 1, 2 or 3 identical or different heteroatoms selected from the group consisting of N, O, and S, which may be substituted, and $R^1$ and $R^2$ are identical or different and each is independently of the other hydroxyl, $C_1$-$C_{20}$-alkoxy, $C_1$-$C_{20}$-alkyl, $C_2$-$C_{20}$-alkenyl, $C_3$-$C_{20}$-alkenyloxy or a radical of the formula II

where $R^3$ is $C_4$-$C_{20}$-alkyl, $C_4$-$C_{20}$-alkenyl or phenylsubstituted $C_1$-$C_{20}$-alkyl, and $R^4$ and $R^5$ are identical or different and each is independently of the other $C_1$-$C_{12}$-alkyl or $OR^3$, where $R^3$ is as defined above.

Further components of the optical recording medium can be for example polymers which are compatible with the compounds of the formula I. Polymers of this type are in general referred to as binders.

Examples of suitable binders are polystyrenes, polyesters, polyacrylates, polymethacrylates, polycarbonates, polyamines, polyvinyl alcohols, polyvinyl chlorides, copolymers of vinyl chloride and vinyl acetate, and polymers or copolymers which contain mesogenic side groups as described in EP-A-90,282 and EP-A-171,045.

In addition, the recording material may contain further suitable additives, such as low molecular weight liquid-crystalline compounds.

Preference is given to an optical recording medium whose radiation-sensitive layer consists only of tetraazaporphyrins of the formula I and of which the dyes are present in the amorphous state.

This term "amorphous" indicates that the radiation-sensitive layer does not have any anisotropic domains larger than a fraction of the thermally changed dimensions, but that the layer is optically isotropic at about 30 nm or higher.

In general, the thickness of the radiation-sensitive layer is from 20 to 400 nm, preferably from 50 to 300 nm.

Preferably, the dyes included in the optical recording medium according to the invention absorb laser light, in particular laser light of the relatively long wavelength (650 to 900 nm).

Preference is given to a recording medium of this type which is based on a disklike base, with or without a reflector layer, and which permits the writing and reproduction of information by means of a semiconductor laser.

An optical storage system so constructed can record high-density information in the form of spiroidal or circularly concentric tracks, fine holes or depressions (about 1 μm in width) which are optically detectable by a change in the reflectivity compared with the surroundings, and it gives good contrast.

Owing to the high light absorption of the dyes, the recording medium according to the invention is very sensitive to the light of the semiconductor laser.

The construction of recording media is known per se.

Suitable bases are for example glass plates or disks or plastics plates or disks, in particular plates or disks made of polymethyl methacrylate, polystyrene, polystyrene copolymers, polyvinyl chloride, polymethylpentene or polycarbonate, with or without tracking grooves.

This base may have the shape of a tape, of a square or rectangular plate or of a round disk, of which the disks 10 or 13 cm in diameter known and customary for laser-optical recording materials are preferred.

In addition, the recording materials may include further layers, such as protective layers, adhesive layers or electrode layers.

Besides the base there may also be present a reflective layer, so that the incident light which passes through the colored layer and is not absorbed is reflected at the reflector layer and passes once more through the colored layer.

Irradiation preferably takes place through a transparent substrate. A possible sequence of layers is then: substrate-absorber layer- (optional reflector).

The base of the light-reflecting layer must have an optically smooth, planar surface which must be so constituted that the absorptive layer firmly adheres thereto. For a positive effect on the surface quality and adhesion phenomena, the base and/or the reflector may be provided with a planarizing layer made of thermosetting or thermoplastic material.

If the radiation-sensitive layer does not have adequate mechanical stability, it may be coated with a transparent protective layer. A number of polymers can be used for this purpose, which, applied by spin coating, knife coating or dip coating of dissolved polymers or vacuum vapor deposition, chiefly in the case of fluorinated polymers, can form a protective layer.

If the data store is constructed from two identical or different recording media in the form of a sandwich, a protective layer can be dispensed with. Besides greater mechanical and rotation-dynamical stability, the sandwich construction offers the advantage of doubled storage capacity.

However, the protective and/or intermediate layers can also be dispensed with if the optical recording medium is of sufficient quality.

The recording medium according to the invention, containing the novel tetraazaporphyrins, strongly absorbs at the semiconductor laser wavelength of from about 650 to 900 nm. The tetraazaporphyrins can be applied in such a way as to produce smooth absorption layers of optical quality into which the information to be stored can be written with a high signal-to-noise ratio.

The absorption materials are preferably applied by spin coating dissolved or dispersed dye with or without binders. Other possible layer formation methods are knife coating and dip coating. Metallic reflection layers for example are preferably applied by vacuum vapor deposition or by mounting suitable metal foils on the base.

To apply the absorption layers from solution, the silicon naphthalocyanine(s) is or are dissolved or dispersed in a suitable solvent, such as cyclohexane, methylcyclohexane, methylene chloride, chloroform, carbon tetrachloride, bromoform, 1,1,1-trichloroethane, 1,1,2-trichloroethane, acetone, methyl ethyl ketone, cyclohexanone, toluene, acetonitrile, ethyl acetate, methanol, ethanol or a mixture thereof, with or without the binder and with or without the addition of an assistant.

This dye preparation is then applied by knife or dip coating but preferably by spin coating to a previously cleaned or subbed surface in layer form and is air dried or cured. The film may also be dried or cured under reduced pressure at elevated temperatures with or without radiation.

As mentioned above, preference is given to a recording medium whose radiation-sensitive layer consists only of tetraazaporphyrins of the formula I, in particular to a recording medium where this layer has been applied by spin coating.

Depending on the construction of the system, first the radiation-sensitive layer is applied and then the reflector, or vice versa. The application of intermediate or protective layers or a reflective layer may, as stated above, also be dispensed with in certain circumstances.

Preference is given to a monolayer system without reflector.

The recording media according to the invention can be written with analog or digital data by means of a write laser beam, analog data being written as is known by means of an analog code modulated continuous wave laser and digital data by means of a pulse code modulated laser.

In general, suitable lasers have at the write wavelength a beam power output of from 1 to 20 mW. The focus diameter of the write laser beam is in general from 300 to 2000 ns. Customarily, the pulse duration on irradiation with a pulse code modulated laser is from 10 to 1000 nm. It is advantageous to use for the writing a laser beam of light of a wavelength which is readily absorbed on the recording layer in question. It is advantageous to use wavelengths of from 400 to 1000 nm.

In the writing operation, the laser beam is guided in a relative motion across the recording material while being perpendicularly incident thereupon and focused on the recording layer. At the point of incidence, the recording layer is locally heated, forming thermally altered areas, for example in the shape of holes, craters or spots. On writing data with pulse code modulated lasers, these areas have essentially a round or oval shape from 100 to 2000 nm in diameter. If written with an analog code modulated continuous wave laser, they can have any desired shape.

The optical recording medium according to the invention is highly suitable for laser-optical data recording.

The data can be written into the recording layer from the base remote side of the layer or through the optically clear base. The latter is of particular advantage.

The written data are read by means of a read laser beam. The power of the read laser beam at the read wavelength is below the threshold at which writing becomes possible. In general, the beam power is from 0.1 to 1.5 mW. It is advantageous to use the laser light of a wavelength which is strongly reflected by the recording layer. The advantageous wavelength ranges from 400 to 1000 nm, in particular from 630 to 900 nm.

In reading, too, the read laser beam is guided in a relative motion across the recording material while being perpendicularly incident thereupon and focused on the recording layer.

If in the course of scanning across the recording layer the read laser beam encounters a thermally altered area, for example a spot, the properties of the light transmitted or reflected by the recording material undergo a change, which is detectable by means of suitable detectors.

This reading of the data in the recording layer can take place from the base remote side of the layer or through the optically clear, transparent base, the latter being of advantage. It is particularly advantageous here to detect the reflected light.

It is also of particular advantage to use for this purpose write and read lasers which emit within the infrared wavelength range from 650 to 900 nm. It is also of advantage here if the write wavelength is identical to the read wavelength or differs only little therefrom. Light of these wavelengths is supplied by customary and known semiconductor lasers.

The recording media according to the invention have numerous special advantages. For instance, their unwritten recording layer is particularly stable, so that it is still highly suitable for a laser-optical data recording even after prolonged storage at comparatively high temperatures and atmospheric humidities. The same is true of the written recording layer; it suffers no information loss even on very prolonged storage. For this reason it is also possible to use write lasers of comparatively low beam power. Moreover, the written recording materials show a particularly high optical contrast between the written and the unwritten areas, which exceeds the previously known optical contrast of written phthalocyanine layers. Furthermore, the novel recording materials permit a bit density of significantly above $10^7$ bits/$cm^2$ and, what is more, the data can be read immediately after having been written.

The tetraazaporphyrins of the formula I according to the invention have further very good application advantages and therefore can also be used for other purposes. More particularly, they can be used for fabricating IR protective layers, IR absorptive films, eyeshade coatings, coatings for automotive windscreens, IR inks, printing inks for IR readable bar codes, liquid crystal displays or IR security systems.

IR readable bar codes are for example bar codes applied to packaging to identify the goods inside.

Liquid crystal displays are the known arrangements which contain layers of liquid-crystalline substances. These layers undergo local changes in optical properties on application of an electrical voltage, which makes it possible to display for example numbers, letters or images.

IR safety systems are arrangements which consist essentially of a laser light source and a suitable detector remote therefrom. The laser beam emitted by the laser light source of this arrangement is incident upon the detector and forms a light barrier. If this barrier is broken, the detector initiates the triggering of an alarm.

Electrophotographic recording materials essentially contain layers which in the dark have a high electrical resistance but on irradiation become conductive. If such layers are electrostatically charged at the surface in the dark and then subjected to imagewise exposure the electrostatic charge in the exposed areas is discharged, the result being an electrostatic image which can be made visible by means of toners.

The Examples which follow serve to illustrate the invention in more detail.

A) Synthesis

EXAMLLE 1 a) Quinoline-2,3-dicarboxamide 30 g of diethyl quinoline-2,3-dicarboxylate were stirred in 200 ml of aqueous ammonia solution (20 % strength by weight) and 100 ml of isopropanol at room temperature for 1 day. The resulting dicarboxamide was filtered off with suction and washed with a little methanol.

b) 2,3-Dicyanoquinoline 9.3 g of the dicarboxamide of a) was introduced in 90 ml of N,N-dimethylformamide. 10 ml of $POCl_3$ were added dropwise at 0° C. The reaction mixture was stirred at room temperature for 20 hours and poured onto ice-water, the resulting mixture was filtered with suction, and the filter residue was washed with water.

Yield: 7.5 g; mp.: 204°–206° C.

c) 4-Aza-1,3-diimino-benzo[f]isoindoline 5 g of the dinitrile, obtained under b) were introduced in 80 ml of methanol, 0.5 g of sodium methoxide was added, and the refluxing mixture was treated with ammonia gas for 12 hours. After cooling down, the product was filtered off with suction and washed with a little methanol.

Yield: 4.5 g; mp.: 230° C.

d) Tetraazaporphyrin of the formula IX ($E^1=E^2=Cl$)

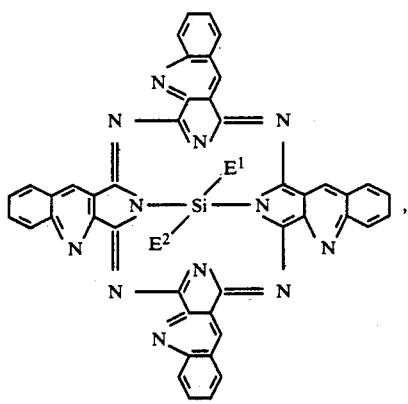

(IX)

4.0 g of the product obtained under c) were heated with 30 ml of tetraline, 4.0 ml of $SiCl_4$ and 15 ml of tributylamine at 230° C. for 6 hours. After cooling, the mixture was diluted with 100 ml of methanol and filtered with suction, and the filter residue was washed with methanol and dried.

Yield: 2.0 g.

e) Tetraazaporphyrin of the formula IX ($E^1=E^2=OH$)

5.0 g of the product obtained under d) were stirred in 100 ml of concentrated sulfuric acid for 20 hours. The reaction mixture was then poured onto ice-water, and the resulting precipitate was filtered off with suction, washed repeatedly with methanol and dried.

Yield: 4.8 g.

f) Tetraazaporphyrin of the formula IX

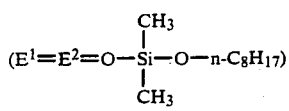

4.0 g of the product obtained under e) were introduced in 150 ml of pyridine. After addition of 5.0 ml of tributylamine and 0.5 g of sodium hydride, the mixture was stirred at 80° C. for 2 hours and then cooled down to room temperature, and 8.5 ml of dimtthyldichlorosilane were added. After stirring overnight, 4.0 ml of n-octanol were added, and the mixture was heated at 80° C. for 6 hours. The bulk of the pyridine was then drawn off under reduced pressure. The residue was stirred up with methanol, filtered off with suction and washed with methanol.

$\lambda_{max}(CH_2Cl_2)$: 724 nm Rf (toluene): 0.75 g) Tetraazaporphyrin of the formula IX

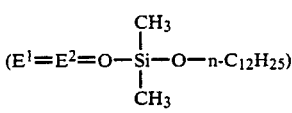

Procedure as per Example f), except the 4.0 ml of n-octanol were replaced by 4.0 ml of n-dodecanol.

$\lambda_{max}(CH_2Cl_2)$: 724 nm Rf (toluene): 0.71

In both cases, the Rf value was determined on silica gel plates from Macherey und Nagel (Polygram 0.2 mm, N-HR UV254).

B) Use

Method for producing a recording medium 1 g of the compound mentioned under f) was stirred in 20 ml of toluene at room temperature overnight and then forced under pressure through a sintered P4 crucible. The resultant solution was then applied by means of a syringe to a rotating disk of polymethyl methacrylate (diameter 12 cm), excess solution being spun off at a speed of 2000 rpm over 25 seconds and the layer then being spun dry at a speed of 5000 rpm over 35 seconds. The layer obtained was homogeneous, pinhole-free and highly reflective.

The layer had reflectance of 35% at 800 nm, 32% at 780 nm and 28% at 750 nm.

In a laser drive, this layer was sensitively writable and readable with a 744 nm laser having a maximum beam power rating of 3.5 mW.

The recording material was stored at 60° C. and a relative humidity of 90 % for ten weeks. During this period, no adverse changes occurred; on the contrary, the recorded data were still readable without error.

We claim:

1. A tetraazaporphyrin of the formula I

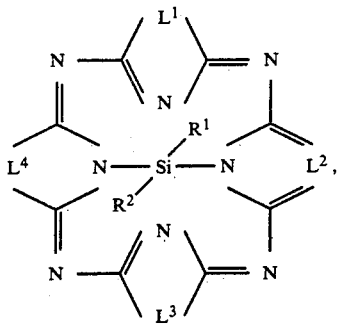
(I)

where $L^1$, $L^2$, $L^3$ and $L^4$ are identical or different and each is independently of the others the radical of a bicyclic aromatic heterocycle of 1, 2 or 3 identical or different heteroatoms selected from the group consisting of N, O and S, which may be substituted, and $R^1$ and $R^2$ are identical or different and each is independently of the other hydroxyl, $C_1$–$C_{20}$-alkoxy, $C_1$–$C_{20}$-alkyl, $C_2$–$C_{20}$-alkenyl, $C_3$–$C_{20}$-alkenyloxy or a radical of the formula II

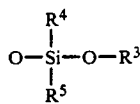
(II)

where $R^3$ is $C_4$–$C_{20}$-alkyl, $C_4$–$C_{20}$-alkenyl or phenyl-substituted $C_1$–$C_{20}$-alkyl, and $R^4$ and $R^5$ are identical or different and each is independently of the other $C_1$–$C_{12}$-alkyl or $OR^3$, where $R^3$ is as defined above.

2. An optical recording medium comprising a base and a radiation-sensitive layer, wherein the radiation-sensitive layer contains a tetraazaporphyrin of the formula I

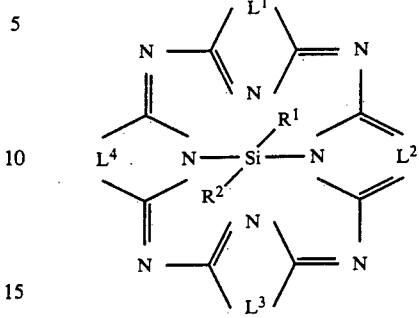
(I)

where $L^1$, $L^2$, $L^3$ and $L^4$ are identical or different and each is independently of the others the radical of a bicyclic aromatic heterocycle of 1, 2 or 3 identical or different heteroatoms selected from the group consisting of N, O and S, which may be substituted, and $R^1$ and $R^2$ are identical or different and each is independently of the other hydroxyl, $C_1$–$C_{20}$-alkoxy, $C_1$–$C_{20}$-alkyl, $C_2$–$C_{20}$-alkenyl, $C_3$–$C_{20}$-alkenyloxy or a radical of the formula II

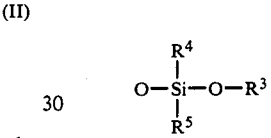
(II)

where $R^3$ is $C_4$–$C_{20}$-alkyl, $C_4$–$C_{20}$-alkenyl or phenyl-substituted $C_1$–$C_{20}$-alkyl, and $R^4$ and $R^5$ are identical or different and each is independently of the other $C_1$–$C_{12}$-alkyl or $OR^3$, where $R^3$ is as defined above.

* * * * *